US00PP33765P2

(12) United States Plant Patent
Thiede

(10) Patent No.: US PP33,765 P2
(45) Date of Patent: Dec. 21, 2021

(54) ***DIANTHUS* PLANT NAMED 'KLEDP20311'**

(50) Latin Name: *Dianthus caryophyllus*
Varietal Denomination: KLEDP20311

(71) Applicant: Klemm+Sohn GmbH & Co. KG, Stuttgart (DE)

(72) Inventor: Lena Thiede, Bempflingen (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/322,478

(22) Filed: May 17, 2021

(51) Int. Cl.
*A01H 5/02* (2018.01)
*A01H 6/30* (2018.01)

(52) U.S. Cl.
USPC ..... Plt./277

(58) Field of Classification Search
USPC ..... Plt./272, 273, 277, 276, 278
See application file for complete search history.

*Primary Examiner* — Susan McCormick Ewoldt
*Assistant Examiner* — Karen M Redden
(74) *Attorney, Agent, or Firm* — Weatherly IP Solutions, LLC; James M. Weatherly

(57) ABSTRACT

A new *Dianthus* plant designated 'KLEDP20311' particularly distinguished by double flowers with a magenta to purple bicolor flower color and a medium amount of filling, is disclosed.

1 Drawing Sheet

Genus and species: *Dianthus caryophyllus*.
Variety denomination: 'KLEDP20311'.

BACKGROUND OF THE NEW PLANT

The present invention comprises a new and distinct variety of *Dianthus*, botanically known as *Dianthus caryophyllus* and hereinafter referred to by the variety name 'KLEDP20311'. 'KLEDP20311' is a selection that resulted from a whole plant mutation of the *Dianthus* line 'KLEDP07088' (unpatented).

In March of 2013, a whole plant mutation of the *Dianthus* line 'KLEDP07088' was discovered in the Netherlands and was subsequently vegetatively propagated by vegetative cuttings. 'KLEDP20311' was found to reproduce true to type in successive generations of asexual propagation via vegetative cuttings in Stuttgart, Germany and Latina, Italy.

SUMMARY

The following are the most outstanding and distinguishing characteristics of 'KLEDP20311' when grown under normal horticultural practices in Latina, Italy and Stuttgart, Germany.

1. Double flowers with a magenta to purple bicolor flower color; and
2. A medium amount of filling.

DESCRIPTION OF THE PHOTOGRAPH

This new *Dianthus* plant is illustrated by the accompanying photographs. The colors shown are as true as can be reasonably obtained by conventional photographic procedures. FIG. 1 shows the whole plant, including the flowers and foliage and buds. The photo was taken in Stuttgart, Germany and are of a 14-week-old plant of 'KLEDP20311'.

DESCRIPTION OF THE NEW VARIETY

The following detailed descriptions set forth the distinctive characteristics of 'KLEDP20311'. The data which define these characteristics were collected from asexual reproductions carried out in Latina, Italy. Data for all characteristics was collected in March of 2021 on plants potted (indoor) in week 38 of 2020. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP20311'.

Parentage: Mutation of variety 'KLEDP07088' (not patented).

Plant:
- *Propagation type*.—Vegetative cuttings.
- *Time to produce a rooted young plant*.—4 weeks.
- *Rooting description and habit*.—Fine white (RHS 155A).
- *Rooting habit*.—Lanceolate.
- *Plant form*.—Upright.
- *Plant height*.—5.0 cm.
- *Plant diameter or spread*.—18.0 cm.

Lateral branches:
- *Length*.—7.0 cm.
- *Diameter*.—0.2 cm.
- *Internode length*.—1.2 cm.
- *Node length*.—0.7 cm.
- *Node diameter*.—0.2 cm.
- *Texture*.—Smooth.
- *Color*.—RHS 138A.

Foliage:
- *Arrangement*.—Opposite.
- *Length*.—5.0 cm.
- *Width*.—0.8 cm.
- *Shape*.—Obovate.
- *Apex*.—Acute.
- *Base*.—Obtuse.
- *Margin*.—Entire.

*Texture* (*both upper and lower surfaces*).—Smooth.

*Immature leaf color*.—Upper surface: RHS146A. Lower surface: RHS147B.

*Mature leaf color*.—Upper surfaces: RHS147A. Lower surface: RHS N137B.

*Venation pattern*.—Parallel.

*Venation color* (*both upper and lower surfaces*).—RHS 144A.

Flowers:

*Flower type and habit*.—Double, round with small sprays.

*Fragrance*.—Sweet.

*Natural flowering season*.—Spring to fall.

*Flower longevity on the plant*.—10 to 20 days.

*Buds*.—Length: 1.8 cm. Diameter: 0.9 cm. Shape: Elliptic. Color: RHS 138A.

*Corolla*.—Quantity of petals per flower/arrangement: 18. Corolla height: 1.5 cm. Petal length: 3.0 cm. Petal width: 1.6 cm. Petal shape: Obtuse. Petal apex: Obtuse. Petal base: Acute. Petal margin: Crenate. Petal texture (both surfaces): Smooth. Petal color, immature and mature. Immature: Upper surface: RHS 67A with 60A center. Lower surface: RHS 63A. Mature: Upper surface: RHS 67A with 59C center. Lower surface: RHS 60C.

*Calyx*.—Quantity of sepals per flower: 5. Calyx height: 1.9 cm. Calyx diameter (at the apex): 0.9 cm. Sepal texture (both upper and lower surfaces): Smooth. Sepal color: Upper surface: RHS 143A. Lower surface: RHS 144C.

Peduncles:

*Length*.—1.0 cm.

*Diameter*.—0.3 cm.

*Strength*.—Strong.

*Texture*.—Smooth.

*Color*.—RHS 137A.

Reproductive organs:

*Stamens*.—Quantity: 5. Filament length: 0.7 cm. Filament color: RHS 2D. Anther length: 0.3 cm. Anther diameter: 0.1 cm. Anther color: RHS 8C. Pollen amount: Not present.

*Pistils*.—Quantity per flower: 2. Pistil length: 1.7 cm. Style length: 0.5 cm. Style color: RHS 155A. Stigma shape: Filamentous. Stigma color: RHS 60A. Ovary size: 0.5 cm. Ovary shape: Elliptic. Ovary color: RHS 145A.

Fruit and seed set: Seed sometimes observed but additional information on seed description is not available.

Disease and pest/insect resistance: No disease and pest/insect resistance observed.

COMPARISON OF 'KLEDP20311' WITH PARENTAL LINE AND KNOWN VARIETY

'KLEDP20311' is distinguished from the parental lines as described in Table 1.

TABLE 1

Comparison with Parental Lines

| Trait | Variety 'KLEDP20311' | Female parent 'KLEDP07088' |
|---|---|---|
| Flower color | Magenta - purple bicolor | White - purple bicolor |

'KLEDP20311' can be compared to the commercial *Dianthus* variety 'KLEDP19309' (U.S. Plant Pat. No. 29,735). Differences between the varieties are described in Table 2.

TABLE 2

Comparison with Similar Variety

| Trait | Variety 'KLEDP20311' | Commercial line 'KLEDP19309' |
|---|---|---|
| Flower color | Magenta - purple bicolor | Dark red white border |
| Amount of filling | Medium | Less than 'KLEDP20311' |

I claim:

1. A new and distinct variety of *Dianthus* plant designated 'KLEDP20311' as illustrated and described herein.

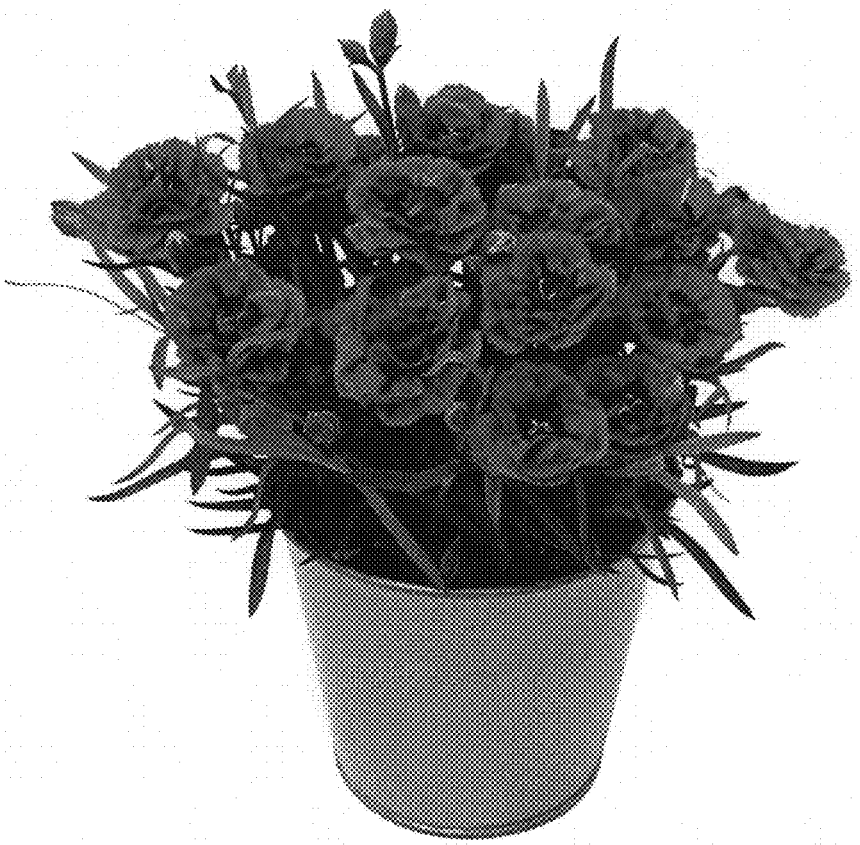

* * * * *